(12) United States Patent
Troxler et al.

(10) Patent No.: US 7,271,168 B2
(45) Date of Patent: Sep. 18, 2007

(54) PIPERAZINE DERIVATIVES HAVING SST1 ANTAGONISTIC ACTIVITY

(75) Inventors: Thomas J. Troxler, Wahlen (CH); Daniel Hoyer, St. Louis (FR)

(73) Assignee: Novartis AG, Basel (CH)

( * ) Notice: Subject to any disclaimer, the term of this patent is extended or adjusted under 35 U.S.C. 154(b) by 232 days.

(21) Appl. No.: 10/494,898

(22) PCT Filed: Nov. 8, 2002

(86) PCT No.: PCT/EP02/12514

§ 371 (c)(1), (2), (4) Date: Oct. 13, 2004

(87) PCT Pub. No.: WO03/040125

PCT Pub. Date: May 15, 2003

(65) Prior Publication Data

US 2006/0079527 A1    Apr. 13, 2006

(30) Foreign Application Priority Data

Nov. 9, 2001    (GB)    .................................. 0127008.1

(51) Int. Cl.
| | | |
|---|---|---|
| *A61K 31/495* | (2006.01) | |
| *A61K 31/496* | (2006.01) | |
| *A61K 31/5025* | (2006.01) | |
| *C07D 295/192* | (2006.01) | |
| *C07D 405/12* | (2006.01) | |
| *C07D 409/12* | (2006.01) | |
| *C07D 487/04* | (2006.01) | |

(52) U.S. Cl. ............ 514/248; 514/253.01; 514/253.12; 514/254.03; 514/254.11; 514/255.01; 544/236; 544/360; 544/364; 544/368; 544/375; 544/380

(58) Field of Classification Search ..................... None
See application file for complete search history.

(56) References Cited

FOREIGN PATENT DOCUMENTS

WO    WO93/01159    1/1993

OTHER PUBLICATIONS

Rolland et al. J. Med. Chem. vol. 48, pp. 6563-6574 (2005).*

* cited by examiner

*Primary Examiner*—Emily Bernhardt
(74) *Attorney, Agent, or Firm*—Peter J. Waibel; Joseph J. Borovian

(57) ABSTRACT

The invention provides compounds of formula (1)

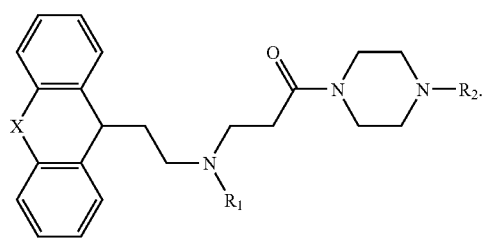

wherein X, $R_1$ and $R_2$ are as defined in the specification, their, preparation and to their use in treating, e.g., depression, anxiety and bipolar disorders.

6 Claims, No Drawings

PIPERAZINE DERIVATIVES HAVING SST1 ANTAGONISTIC ACTIVITY

The present invention relates to piperazine derivatives, their preparation, their use as pharmaceuticals and pharmaceutical compositions comprising them.

More particularly the present invention provides a compound of formula I

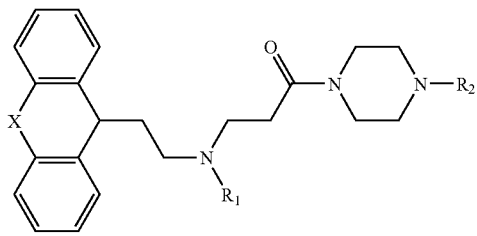

I wherein
X is a single bond or —O—, —S—, —CH$_2$—, —CH═CH— or —CH$_2$—CH$_2$—,
R$_1$ is (C$_{1-4}$)alkyl, (C$_{2-5}$)alkenyl or (C$_{3-7}$)cycloalkyl(C$_{1-4}$)alkyl, and
R$_2$ is a group of formula

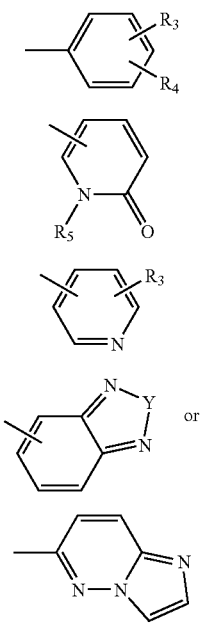

wherein
Y is —O— or S—,
R$_3$ and R$_4$, independently, are hydrogen, hydroxy, halogen, nitro, cyano, trifluoromethyl, (C$_{1-4}$)alkyl or (C$_{1-4}$)alkoxy, and
R$_5$ is hydrogen or (C$_{1-4}$)alkyl, in free base or acid addition salt form Halogen is fluorine, chlorine, bromine or iodine, preferably fluorine or chlorine.

The above-defined alkyl and alkoxy groups preferably represent methyl and methoxy.

In a further aspect the invention provides a process for the production of the compounds of formula I and their acid addition salts, whereby a compound of formula II

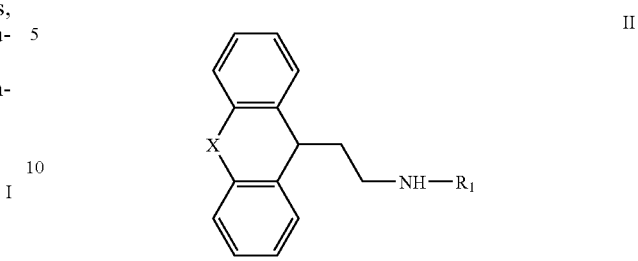

II wherein X and R$_1$ are as defined above, is reacted with a compound of formula III

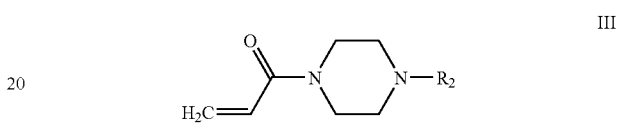

III wherein R$_2$ is as defined above, and the compounds of formula I thus obtained are recovered in free base or acid addition salt form.

The reaction can be effected according to conventional procedures, e.g. as described in Example 1.

Alternatively, the compounds of formula I and their acid addition salts can be produced over a process whereby a compound of formula IV

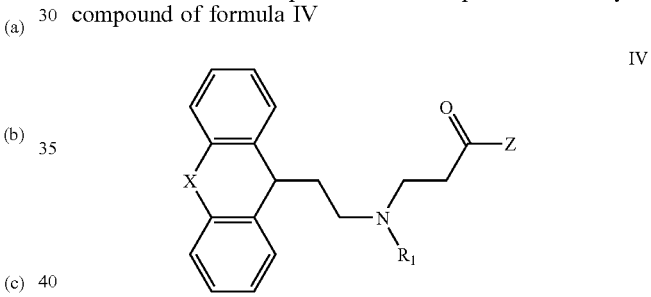

IV wherein X and R$_1$ are as defined above and Z is hydroxy, halogen or OM, M being an alkali metal, is reacted with a compound of formula V

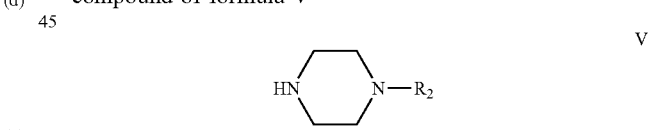

V wherein R$_2$ is as defined above, and the compounds of formula I thus obtained are recovered in free base or acid addition salt form In formula IV, Z as halogen is for example chlorine and, as an alkali metal, for example sodium.

The reaction can be effected according to known amide formation methods. When Z in formula IV is hydroxy, a corresponding compound in which Z is halogen, for example chlorine, may first be prepared and then reacted with the compound of formula V, for example as described in Example 2.

Working up the reaction mixtures according to the above processes and purification of the compounds thus obtained may be carried out in accordance to known procedures.

Acid addition salts may be produced from the free bases in known manner, and vice versa. Suitable acid addition salts for use in accordance with the present invention include for example the hydrochloride.

The starting compounds of formula I may be produced by reduction of compounds of formula VI

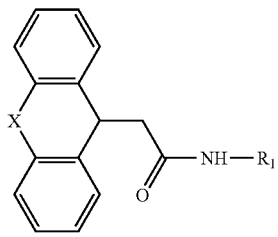

VI wherein X and R₁ are as defined above, obtained by amide formation from acids of formula VII

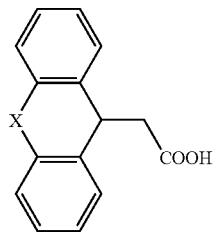

VII wherein X is as defined above. The reactions may be carried out in known manner, e.g. as described in Example 1, b) and c).

The starting compounds of formula III may be produced by reaction of compounds of formula V with acryloyl chloride, e.g. as described in Example 1 d).

The starting compounds of formula IV may be produced from known compounds using conventional procedures. For example compounds of formula IV wherein Z is chlorine may be, produced according to the following reaction scheme. All the reactions in this scheme may be carried out in known manner, e.g. as described in Example 2.

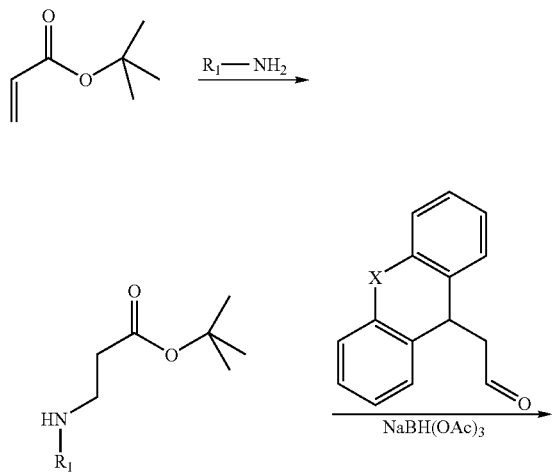

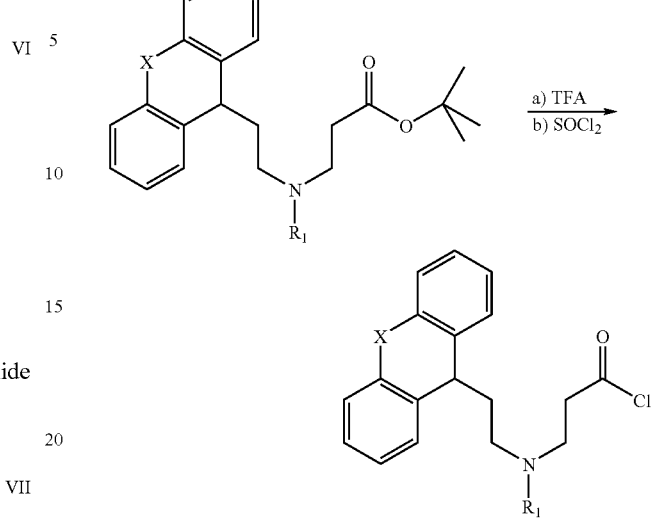

The starting compounds of formulae V and VII are known or may be produced in analogous manner to known procedures, e.g. as described in Example 1 a) for the compounds of formula VII.

Compounds of formula I and their pharmaceutically acceptable acid addition salts, hereinafter referred to as agents of the invention, exhibit valuable pharmacological properties when tested in vitro using SRIF receptor expressing cell cultures and in animals, and are therefore useful as pharmaceuticals.

In particular the agents of the invention bind to somatostatin receptors. More particularly they are selective antagonists at Somatostatin $sst_1$ receptors, previously called SSTR-1 receptors (see Hoyer et al., TiPS, 1995, 16; 86-88), as determined in radioligand binding and second messenger studies [see for example K Kaupmann et al., FEBS LETTERS 1993, 331: 53-59] where they exhibit selective affinity for $sst_1$ receptors with $pIC_{50}$ values between about 7.5 and 9.5.

The agents of the invention are therefore useful for treatment in anxiety, depression, schizophrenia, neurodegenerative diseases such as dementia, for the treatment of tumors and for vascular disorders and immunological diseases, as confirmed in a range of standard tests as indicated below:

At doses of about 0.3 to 3 mg/kg p.o., the agents of the invention increase exploratory behavior of mice in the open half of the half enclosed platform, a model which is predictable for anxiolytic activity (Psychopharmacology, 1986, 89:31-37).

In the same half enclosed platform model, the agents of the invention at the above indicated doses also increase vigilance of the mice. The compounds are therefore indicated for the treatment of depression, schizophrenia and dementia, in particular of senile dementia of the Alzheimer type (SDAT).

In the intruder mouse test [Triangle, 1982, 21: 95-105; J. Clin. Psychiatry, 1994, 55:9 (suppl. B) 4-7], the agents of the invention increase social investigation and reduce defensive ambivalence in the treated intruder mouse at doses of about 1 to about 10 mg/kg s.c., suggesting an antidepressant profile like carbamazepine and lithium, a neuroleptic profile like clozapine and an anxiolytic profile like diazepam.

Furthermore at said doses the agents of the invention reduce aggressive behaviour (attacks, chases, bites) in the Matched Pairs Situation test in mice [Dixon et al., J. Clin. Psychiatry 55: (9) [Suppl. B] 4-7 (1994)]. Since as mentioned above they additionally attenuate defensive behaviours in the intruder mouse test, the agents of the invention exhibit an ethopharmacological profile which is very similar to that of carbamazepine, lithium chloride and clozapine. They are therefore indicated for the treatment of affective disorders including bipolar disorders e.g. manic-depressive psychoses, extreme psychotic states e.g. mania, schizophrenia, and excessive mood swings where behavioural stabilization is desired. In addition, the compounds are indicated in anxiety states, generalized anxiety as well as social stress and agoraphobia, as well as those behavioural states characterized by social withdrawal e.g. negative symptoms.

Moreover when given at doses of about 0.03 to 3 mg/kg p.o. to rodents, the agents of the invention counteract electroshock-induced amnesia, increase retention performance in a passive avoidance paradigm (Mondadori et. al., Pharmacology Communications 1992, 2: 93-97) and improve social recognition (Mondadori et al., Behavioural Brain Research 1996, 77: 227-229). The compounds are therefore indicated for the treatment of cognitive disturbances and learning/memory disorders.

The positive effects on memory acquisition/retention combined with the sociotropic and antiaggressive components displayed by the agents of the invention, suggest that these will prove useful in the treatment of ADHD (attention deficit and hyperactivity disorders).

The agents of the invention are also effective in the treatment of various kinds of tumors, particularly of $sst_1$ receptor bearing tumors, as indicated in proliferation tests with various different cancer cell lines and in tumor growth experiments in nude mice with hormone-dependent tumors [see for example: G. Weckbecker et al., Cancer Research 1994, 54: 6334-6337]. Thus the compounds are indicated in the treatment of, for example, cancers of the breast, the prostate, the colon, the pancreas, the brain and the lung (small cell lung cancer).

For all the above mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 10 mg/kg animal body weight. In larger mammals, for example humans, an indicated daily dosage is in the range from about 5 to about 200 mg, preferably about 10 to about 100 mg of the compound conveniently administered in divided doses up to 4 times a day or in sustained release form.

The agents of the invention may be administered in free form or in pharmaceutically acceptable salt form. Such salts may be prepared in conventional manner and exhibit the same order of activity as the free compounds.

Accordingly in a further aspect the present invention provides the agents of the invention for use as pharmaceuticals, more specifically for treatment in the above-mentioned conditions, e.g. depression, anxiety and bipolar disorders.

The present invention furthermore provides a pharmaceutical composition comprising an agent of the invention in association with at least one pharmaceutically acceptable diluent or carrier. Such compositions may be formulated in conventional manner. Unit dosage forms contain, for example, from about 0.25 to about 50 mg of an agent according to the invention.

Agents of the invention may be administered by any conventional route, for example parenterally e.g. in form of injectable solutions or suspensions, or enterally, preferably orally, e.g. in the form of tablets or capsules.

The agents of the invention may alternatively be administered e.g. topically in the form of a cream, gel or the like, or by inhalation, e.g. in dry powder form.

Examples for compositions comprising an agent of the invention include, e.g. a solid dispersion, an aqueous solution, e.g. containing a solubilising agent, a microemulsion and a suspension of an agent of the invention. The composition may be buffered to a pH in the range of e.g. from 3.5 to 9.5, by a suitable buffer.

The agents of the invention can be administered either alone or in combination with other pharmaceutical agents effective in the treatment of conditions mentioned above.

Thus, the agents of the invention can be used for the treatment of depressive symptoms in combination with: tricyclics, MAO inhibitors, SSRI's, SNRI's, NK receptor antagonists, CRF-receptor antagonists, $5HT_7$ receptor-antagonists, mGlu receptor agonists/antagonist/modulators, GABA-$_A$ or GABA-$_{A/B}$ receptor agonist/antagonists or modulators, vasopressin receptor antagonists, electroconvulsive shock, sleep deprivation, or herbal medicine such as St. John's Wort.

The agents of the invention can also be used for the treatment of anxiety-symptoms in combination with: benzodiazepines including mitochondrial benzodiazepine-ligands, 5-$HT_{1A}$ receptor agonists, SSRI's, SNRI's, NK receptor-antagonists, CRF receptor-antagonists, vasopressin receptor-antagonists, mGlu receptor agonists/antagonist/modulators, GABA-$_A$ or GABA-$_{A/B}$ receptor agonists/antagonists or modulators.

The agents of the invention can further be used for the treatment of any forms of dementia, including Alzheimer's disease (SDAT) in combination with: acetylcholine-esterase inhibitors, such as rivastigmine and donepezil, mixed acetylcholine/butyrylcholine esterase-inhibitors and nicotinic-alpha$_7$-receptor agonists.

Moreover the agents of the invention can be used for the treatment of psychotic symptoms, including positive and negative symptoms in schizophrenia and schizoid type syndromes in combination with: any typical or atypical antipsychotic, such as clozapine or haloperidol, and nicotinic-alpha$_7$-receptor agonists.

Furthermore the agents of the invention can be used for the treatment of bipolar disorders in combination with: any antimanic agent (e.g. Lithium, Carbamazepine, Valproate) or any atypical or typical antipsychotic.

The pharmaceutical compositions for separate administration of the combination partners and for the administration in a fixed combination, i.e. a single galenical composition comprising at least two combination partners according to the invention, can be prepared in a manner known per se and are thus suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

In particular, a therapeutically effective amount of each of the combination partners may be administered simultaneously or sequentially and in any order, and the components may be administered separately or as fixed combination.

Accordingly the invention also provides a combination comprising a therapeutically effective amount of an agent of the invention and a second drug substance, said second drug substance being for example for use in any of the particular indications hereinbefore set forth.

The preferred indications are depression, anxiety and affective disorders, including bipolar disorders, e.g. mania.

In accordance with the foregoing, the present invention also provides the use of an agent of the invention as a pharmaceutical, e.g. for the treatment of depression, anxiety and bipolar disorders.

Moreover the present invention provides the use of an agent of the invention for the manufacture of a medicament for the treatment of any condition mentioned above, e.g. depression, anxiety and affective disorders.

In still a further aspect the present invention provides a method for the treatment of any condition mentioned above, e.g. depression, anxiety and bipolar disorders, in a subject in need of such treatment, which comprises administering to such subject a therapeutically effective amount of an agent of the invention.

Preferred compounds according to the invention include 1-[4-(3,4-difluoro-phenyl)-piperazin-1-yl]-3-{methyl-[2-(9H-xanthen-9-yl)-ethyl]-amino}-propan-1-one (compound A) and 1-[4-(3,4-difluoro-phenyl)-piperazin-1-yl]-3-{[2-(9H-fluoren-9-yl)-ethyl]-methyl-amino}-propan-1-one (compound B), in free base or acid addition salt form.

Both compounds A and B have high affinty for somatostatin receptors, independently of the species, the expression system and the radioligand used, and are $sst_1$ selective. The following pKd values have been found:

Compound A: human 8.3-8.8; mouse 8.0-8.4; rat 9.1.
Compound B: human 8.2-8.6; mouse 8.3-8.6; rat 9.3.

In the above-mentioned intruder test, both compounds A and B significantly increase the duration of social contacts of the intruder rat towards the resident rat. In the social recognition test in mice, both compounds exhibit a specific enhancing effect on the learning/memory performance.

The following examples illustrate the invention. The temperatures are given in degrees Celsius and are uncorrected.

EXAMPLE 1

1-[4-(3,4-Difluoro-phenyl)-piperazin-1-yl]-3-{methyl-[2-(9H-xanthen-9-yl)-ethyl]-amino}-propan-1-one a) (9H-Xanthen-9-yl)-acetic acid To glacial acetic acid (375 ml) in a 2 l round bottom flask is added 9H-xanthen-9-ol (25 g, 126 mmol) and malonic acid (25 g, 240 mmol). The clear yellow-brown solution is stirred for 2 h and left standing over night (15 h). The solution is then diluted with ice cold water (1 l) which leads to a precipitation. The precipitate is collected by filtration and washed with cold water (3×200 ml). The solid is transferred with the help of little water (130 ml) to a 2 l round bottom flask containing 50% $K_2CO_3$ (276 g) and heated to reflux for 20'. The slightly turbid solution is cooled to 50° and filtered through Hyflo. The clear brownish solution is added slowly and with good stirring to a mixture of conc. HCl (200 ml) and ice water (800 ml) (evolution of $CO_2$!). The precipitate is collected by filtration, washed with water and dried in vacuo at 80°. The malonic acid intermediate thus obtained (31 g as a greenish powder) is dissolved in pyridine (250 ml) and heated to reflux for 2 h. The clear, brownish solution is then cooled to 0° and added with good stirring to a mixture of conc. HCl (300 ml) and ice water (700 ml). The precipitate that is formed is collected by filtration and washed with water. The solid is dissolved in $Et_2O$, the water layer separated, the organic layer dried with $Na_2SO_4$, filtered and evaporated to a volume of about 150 ml. When crystallization starts, the mixture is cooled to 0°, diluted with hexane (250 ml) and left at −20° for three days. The solid product is collected by filtration, washed with hexane and dried in vacuo at 80° to afford (9H-xanthen-9-yl)-acetic acid (25.2 g, 83%) as off-white crystals.

b) N-Methyl-2-(9H-xanthen-9-yl)-acetamide

To a solution of (9H-xanthen-9-yl)-acetic acid (4.8 g, 20 mmol) in THF (50 ml) is added with stirring 1,1'-carbonyldiimidazole (3.57 g, 22 mmol), and stirring continued for 2 h. The suspension that is formed is cooled to −20° and neat methylamine (1.55 g, 2.2 ml, 50 mmol) is added. The white suspension is stirred for 15 h at room temperature. All volatiles are removed in vacuo, and $CH_2Cl_2$ (150 ml) and water (50 ml) is added to the residue. The phases are separated and the organic phase consecutively washed with a 1:1 mixture of 2 N HCl and brine (50 ml), brine (50 ml) and a 1:1 mixture of 1 M $NaHCO_3$ and brine (50 ml). Drying over $Na_2SO_4$, filtration and evaporation of the solvent affords N-methyl-2-9H-xanthen-9-yl)-acetamide (4.82 g, 95%) as a white solid, that is sufficiently pure for the next step.

c) Methyl-[2-(9H-xanthen-9-yl)-ethyl]-amine

To a suspension of $LiAlH_4$ (2.59 g, 68.21 mmol) in THF (200 ml) under Argon is added dropwise a solution of $CHCl_3$ (2.71 g, 22.74 mmol) in THF (15 ml) at room temperature over 15'. Stirring is continued for 30' at the same temperature. Within 15', a solution of N-methyl-2-(9H-xanthen-9-yl)-acetamide (4.80 g, 18.95 mmol) in THF (150 ml) is added. The mixture is stirred for 1 h at room temperature and then heated to reflux for 1 h. After cooling to 0°, 2 N NaOH (10 ml) is added dropwise under vigorous stirring. Filtration over Hyflo and evaporation of the filtrate affords a yellowish oil (4.88 g), which is dissolved in $Et_2O$ (50 ml), and the turbid solution filtered over Hyflo. Evaporation of the solvent affords crude methyl-[2-(9H-xanthen-9-yl)-ethyl]-amine (4.76 g, quant.) as a yellowish, clear oil that is used without further purification.

d) 1-[4-(3,4-Difluoro-phenyl)-piperazin-1-yl]-propenone

To a mixture of 1-(3,4-difluoro-phenyl)-piperazine (9.9 g, 50 mmol) in $CH_2Cl_2$ (150 ml) and 1 M aqueous $NaHCO_3$ (100 ml, 100 mmol) at 5-10° is added dropwise and under vigorous stirring a solution of acryloyl chloride (5.43 g, 60 mmol) in $CH_2Cl_2$ (50 ml), and then stirred for 1 h at room temperature. The phases are separated, the organic phase dried over $Na_2SO_4$ and the solvent evaporated to afford 13.0 g of the crude product as a yellow-brownish oil. It is dissolved in $Et_2O$ (70 ml), which leads spontaneously to crystallization. The mixture is kept at 0° for 1 h, the crystals collected by filtration, washed with cold $Et_2O$ (−20°) and dried in vacuo at 50° to afford 1-[4-(3,4-difluoro-phenyl)-piperazin-1-yl]-propenone (9.84 g, 78%) as a yellow-brownish powder which melts at 90-96°.

e) 1-[4-(3,4-Difluoro-phenyl)-piperazin-1-yl]-3-{methyl-[2-(9H-xanthen-9-yl)-ethyl]-amino}-propan-1-one A solution of methyl-[2-(9H-xanthen-9-yl)-ethyl]-amine (4.76 g, 18.95 mmol) and 1-[4-(3,4-difluoro-phenyl)-piperazin-1-yl]-propenone (4.78 g, 18.95 mmol) in THF (10 ml) is stirred at 40-45° for 24 h. The reaction mixture is directly charged on a chromatography column (430 g silicagel). Elution with EtOAc and then EtOAc/MeOH 4:1 affords a yellowish oil (7.1 g) that is dissolved in MTBE (70 ml) and briefly boiled with activated charcoal (1 g). Filtration and evaporation affords the product base as a slightly yellowish oil (7.07 g, 76%). This oil (14.38 mmol) is dissolved in warm MeOH (35 ml) and treated with fumaric acid (835 mg, 7.19 mmol). The clear solution is diluted with $Et_2O$ (250 ml), slowly cooled to −20° and left for crystallization at this temperature over night. Collection of the crystals by filtration, washing with cold $Et_2O$/MeOH 10:1 and drying in vacuo at 60° affords the fumarate salt (6.9 g, 66%) as small white plates that melt at 156-158°. Recrystallization from MeOH (50 ml) and $Et_2O$ (300 ml) affords 1-[4-(3,4-difluoro-phenyl)-piperazin-1-yl]-3-{methyl-[2-(9H-xanthen-9-yl)-ethyl]-amino}-propan-1-one fumarate salt (6.50 g, 62%) with a melting point of 158-161°.

EXAMPLE 2

1-[4-(3,4-Difluoro-phenyl)-piperazin-1-yl]-3-{[2-(9H-fluoren-9-yl)-ethyl]-methyl-amino}-propan-1-one a) 3-Methylamino-propionic acid tert-butyl ester A 33% solution of methylamine in EtOH (62 ml) is cooled to 0°. A solution of tert-butyl acrylate (12.8 g) in EtOH (50 ml) is added dropwise over 2.5 hours. This mixture is allowed to reach room temperature over night. All volatiles are removed under reduced pressure and the residue chromatographed on silicagel using first EtOAc and then EtOAc/MeOH 1:1 as eluent. 7.81 g of a slightly yellow oil are obtained. TLC (silicagel, EtOAc/MeOH 1:1): rf 0.13.

b) 3-{[2-(9H-fluoren-9-yl)-ethyl]-methyl-amino}-propionic acid tert-butyl ester

A solution of 3-methylamino-propionic acid tert-butyl ester (6.21 g) and (9H-fluoren-9-yl)-acetaldehyde (8.14 g) in 1,2-dichloroethane (135 ml) is stirred under argon. Sodium triacetoxy borohydride (9.57 g) is added and the mixture stirred for 2.5 hours at room temperature. The clear solution is then treated with 1 M aq. $NaHCO_3$ under vigorous stirring for 10 minutes. The organic phase is dried over sodium sulfate, filtered and evaporated. The crude product is crystallized from hexane to afford 11.8 g of an off-white solid. M.p. 64°-65°. TLC (silicagel, heptane/dichloromethane/ethanol 65:40:20): rf 0.44.

c) 3-{[2-(9H-fluoren-9-yl)-ethyl]-methyl-amino}-propionic acid

A solution of 3-{[2-(9H-fluoren-9-yl)-ethyl]-methyl-amino}-propionic acid tert-butyl ester (11.4 g) in 20 ml dichloromethane is cooled to 0°. Trifluoroacetic acid (20 ml) is added and the solution stirred at room temperature over night. To this mixture a 1 M aq. $NaHCO_3$ solution (262 ml) is added dropwise under vigorous stirring. The phases are separated, the water phase acidified with 14 ml 2N HCl and extracted several times with dichloromethane. The combined extracts are dried over sodium sulfate, filtered and evaporated to afford 11.4 g (100%) of a light brown foam which is used without purification. TLC (silicagel, dichloromethane/methanol 85:15): rf 0.3.

d) 3-{[2-(9H-fluoren-9-yl)-ethyl]-methyl-amino}-propionic acid chloride hydrochloride A solution of 3-{[2-(9H-fluoren-9-yl)-ethyl]-methyl-amino}-propionic acid (11.4 g) in dichloroethane (115 ml) is treated with thionyl chloride (7.71 g) at room temperature for 5' and at 60° for 1 hour. About 20 ml volatiles are removed under reduced pressure. 100 ml diethyl ether are added and the mixture kept at 5° over night for crystallization. The crystals are collected by filtration, washed with dichloroethane/diethylether and dried. M.p. 120°-123°.

e) 1-[4-(3,4-Difluoro-phenyl)-piperazin-1-yl]-3-{[2-(9H-fluoren-9-yl)-ethyl]-methyl-amino}-propan-1-one dihydrochloride A mixture of 3-{[2-(9H-fluoren-9-yl)-ethyl]-methyl-amino}-propionic acid chloride hydrochloride (1.14 g), 4-(3,4-Difluoro-phenyl)-piperazine (587 mg), dichloromethane (25 ml) and 1 M aq. $K_2CO_3$ (25 ml) is stirred at room temperature for 1 hour. The phases are separated, the organic phase dried over sodium sulfate, filtered and evaporated. Purification by chromatography on silicagel (EtOAc/MeOH 7:3) afforded 1.2 g (100%) of a slightly colored oil. It is dissolved in 4 ml MeOH and acidified with 6 ml 1 M HCl in diethyl ether. More ether is added until the solution gets cloudy (ca. 3 ml). Crystallization at 5° afford 1.01 g (74%) of the desired product as dihydrochloride. M.p. 144°-154°. Anal: Calculated. for $C_{29}H_{33}Cl_2F_2N_3O.H_2O$: C, 61.48%; H, 6.22%; N, 7.41%. Found: C, 61.52%; H, 6.36%; N, 7.37%.

| Example | X | $R_1$ | $R_2$ | salt form | M.p. |
| --- | --- | --- | --- | --- | --- |
| 3 | bond | -Me | 4-pyridyl | free base | 90-95° |
| 4 | bond | -Me | benzo[1,2,5]oxadiazol-5-yl | 0.5 fumarate | 183-185° |
| 5 | bond | -Me | imidazo[1,2-b]pyridazin-6-yl | 1 fumarate | 212-213° |
| 6 | bond | -Me | 4-nitrophenyl | 2 HCl | 109-111° |
| 7 | —S— | -Me | 4-nitrophenyl | 2 HCl | 104-110° |
| 8 | —O— | -Me | 4-nitrophenyl | free base | 135-139° |
| 9 | —CH=CH— | -Me | 4-nitrophenyl | free base | 48-52° |
| 10 | —$CH_2$—$CH_2$— | -Me | 4-nitrophenyl | 2 HCl | 58-70° |
| 11 | bond | -Et | 4-nitrophenyl | 2 HCl | 185-189° |
| 12 | bond | -isopropyl | 4-nitrophenyl | free base | 98-100° |
| 13 | bond | -allyl | 4-nitrophenyl | free base | 82-84° |
| 14 | bond | -cyclopropylmethyl | 4-nitrophenyl | free base | 119-121° |
| 15 | —O— | -Me | benzo[1,2,5]oxadiazol-5-yl | 0.5 fumarate | 160-161° |
| 16 | —O— | -Me | benzo[1,2,5]thiadiazol-5-yl | free base | oil |
| 17 | —O— | -Me | 1-methyl-6-oxo-1,6-dihydro-pyridin-2-yl | free base | oil |

Me = methyl; Et = ethyl

The invention claimed is:
1. A compound of formula I

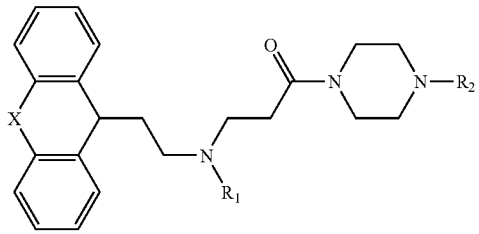

wherein
X is a single bond or —O—, —S—, —CH$_2$—, —CH=CH— or —CH$_2$—CH$_2$—,
R$_1$ is (C$_{1-4}$)alkyl, (C$_{2-5}$)alkenyl or (C$_{3-7}$)cycloalkyl(C$_{1-4}$)alkyl, and
R$_2$ is a group of formula (a) 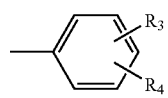

(b) 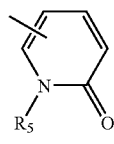

(c) 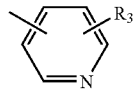

(d) 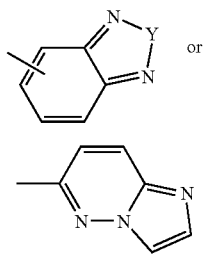 or (e) 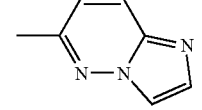

wherein
Y is —O— or —S—,
R$_3$ and R$_4$, independently, are hydrogen, hydroxy, halogen, nitro, cyano, trifluoromethyl, (C$_{1-4}$)alkyl or (C$_{1-4}$)alkoxy, and
R$_5$ is hydrogen or (C$_{1-4}$)alkyl, in free base or acid addition salt form.

2. A compound according to claim 1 which is 1-[4-(3,4-difluoro-phenyl)-piperazin-1-yl]-3-{methyl-[2-(9H-xanthen-9-yl)-ethyl]-amino}-propan-1-one in free base or acid addition salt form.

3. A compound according to claim 1 which is 1-[4-(3,4-difluoro-phenyl)-piperazin-1-yl]-3-{[2-(9H-fluoren-9-yl)-ethyl]-methyl-amino}-propan-1-one in free base or acid, addition salt form.

4. A process for the preparation of a compound of formula I as defined in claim 1, or a salt thereof, which includes the step of reacting a compound of formula II

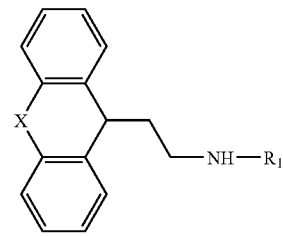

wherein X and R$_1$ are as defined in claim 1, with a compound of formula III

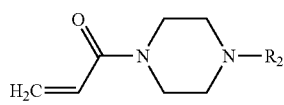

wherein R$_2$ is as defined in claim 1, or reacting a compound of formula IV

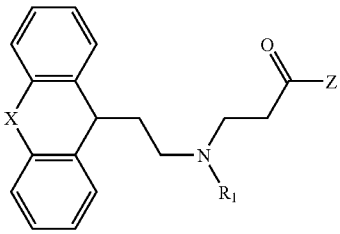

wherein X and R$_1$ are are as defined in claim 1 and Z is hydroxy, halogen or OM, M being an alkali metal, with a compound of formula V

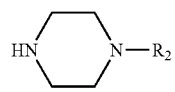

wherein R$_2$ is as defined in claim 1, and recovering the thus obtained compound of formula I in free base or acid addition salt form.

5. A pharmaceutical composition comprising a compound of claim 1 in free base of pharmaceutically acceptable acid addition salt form, in association with a pharmaceutical carrier or diluent.

6. A method for the treatment of depression, anxiety and bipolar disorders in a subject in need of such treatment, which comprises administering to such subject a therapeutically effective amount of a compound of claim 1 in free base or pharmaceutically acceptable acid addition salt form.

* * * * *